US010172672B2

(12) United States Patent
Jadhav

(10) Patent No.: US 10,172,672 B2
(45) Date of Patent: Jan. 8, 2019

(54) JAW FORCE CONTROL FOR ELECTROSURGICAL FORCEPS

(71) Applicant: COVIDIEN LP, Mansfield, MA (US)

(72) Inventor: Amarsinh D. Jadhav, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 387 days.

(21) Appl. No.: 14/992,075

(22) Filed: Jan. 11, 2016

(65) Prior Publication Data

US 2017/0196620 A1   Jul. 13, 2017

(51) Int. Cl.
*A61B 17/28* (2006.01)
*A61B 18/14* (2006.01)
(Continued)

(52) U.S. Cl.
CPC .......... *A61B 18/1445* (2013.01); *A61B 17/28* (2013.01); *A61B 17/2804* (2013.01);
(Continued)

(58) Field of Classification Search
CPC .. A61B 2018/0053; A61B 2018/00184; A61B 2018/00297; A61B 2018/00601; A61B 2018/0063; A61B 2018/0091; A61B 2018/0231; A61B 2018/1457; A61B 18/04; A61B 18/085; A61B 18/1402; A61B 18/1442; A61B 18/1445; A61B 17/28;
(Continued)

(56) References Cited

U.S. PATENT DOCUMENTS

D249,549 S   9/1978  Pike
D263,020 S   2/1982  Rau, III
(Continued)

FOREIGN PATENT DOCUMENTS

CN   201299462        9/2009
DE   2415263 A1      10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003. (4 pages).
(Continued)

*Primary Examiner* — Ronald Hupczey, Jr.
*Assistant Examiner* — Bradford C Blaise

(57) ABSTRACT

A surgical instrument includes a first shaft, a second shaft, and a hinge. The first shaft includes a proximal handle and a distal jaw member. The second shaft includes a first segment that has a proximal handle and a second segment that has a distal jaw member. One of the first and second shafts is pivotal relative to the other to pivot the jaw members between an open configuration where the jaw members are spaced relative to one another and an activatable configuration where the jaw members are closer to one another and suitable for applying electrosurgical energy to tissue disposed therebetween. The hinge couples the first and second segments to one another. The first and second segments have a straight configuration where the first and second segments align with a longitudinal axis and a pivoted configuration where the second segment is disposed at an angle relative to the longitudinal axis.

18 Claims, 4 Drawing Sheets

(51) Int. Cl.

| | | |
|---|---|---|
| A61B 18/00 | (2006.01) | |
| A61B 17/00 | (2006.01) | |
| A61B 18/04 | (2006.01) | |
| A61B 17/29 | (2006.01) | |
| A61B 18/08 | (2006.01) | |
| A61B 18/02 | (2006.01) | |
| A61B 90/00 | (2016.01) | |

(52) U.S. Cl.
CPC ....... A61B 17/2833 (2013.01); A61B 17/2841 (2013.01); A61B 17/29 (2013.01); A61B 18/04 (2013.01); A61B 18/085 (2013.01); A61B 18/1402 (2013.01); A61B 2017/0042 (2013.01); A61B 2017/2901 (2013.01); A61B 2017/2946 (2013.01); A61B 2018/00053 (2013.01); A61B 2018/0063 (2013.01); A61B 2018/0091 (2013.01); A61B 2018/00184 (2013.01); A61B 2018/00297 (2013.01); A61B 2018/00601 (2013.01); A61B 2018/00607 (2013.01); A61B 2018/00642 (2013.01); A61B 2018/0231 (2013.01); A61B 2018/1457 (2013.01); A61B 2090/032 (2016.02); A61B 2090/035 (2016.02)

(58) Field of Classification Search
CPC . A61B 17/2804; A61B 17/2841; A61B 17/29; A61B 17/3201; A61B 17/44; A61B 17/22031; A61B 10/06; A61B 90/00; A61B 90/03; A61B 17/2833; A61B 2017/00619; A61B 2017/2837; A61B 2017/2946; B25B 7/00; B25B 7/14; B25B 7/16; B25B 7/123
USPC ......................................... 606/41, 49, 50, 51
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,562,699 A * | 10/1996 | Heimberger ....... A61B 17/2841 600/564 |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| 7,234,377 B2 * | 6/2007 | Wolfson ............... B25B 7/00 81/415 |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 2010/0063525 A1 | 3/2010 | Beaupre et al. |
| 2010/0063526 A1 | 3/2010 | Beaupre et al. |
| 2010/0063527 A1 | 3/2010 | Beaupre et al. |
| 2013/0018364 A1 | 1/2013 | Chernov et al. |
| 2013/0018411 A1 * | 1/2013 | Collings ............... A61B 17/285 606/205 |
| 2013/0190753 A1 * | 7/2013 | Garrison ................ A61B 17/29 606/41 |
| 2013/0245421 A1 * | 9/2013 | Andrus ................ A61B 5/062 600/409 |
| 2014/0214019 A1 * | 7/2014 | Baxter, III ......... A61B 18/1442 606/33 |
| 2014/0336635 A1 * | 11/2014 | Hart .................... A61B 17/2804 606/41 |
| 2015/0164526 A1 * | 6/2015 | Bernhardt ............... B26B 13/12 606/205 |
| 2017/0119416 A1 * | 5/2017 | Sajid .................. A61B 17/2841 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |

(56) References Cited

FOREIGN PATENT DOCUMENTS

| | | |
|---|---|---|
| EP | 1159926 A3 | 3/2003 |
| JP | 61-501068 | 9/1984 |
| JP | 10-24051 A | 1/1989 |
| JP | 11-47150 A | 6/1989 |
| JP | 6502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |
| WO | WO 2016028980 A1 * | 2/2016 ......... A61B 18/1442 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).

Seyfan et al. "Sutureless Closed Hemorrhoidectomy: A New Technique" Annals of Surgery vol. 234 No. 1, Jul. 2001 pp. 21-24.

Levy et al., "Update on Hysterectomy—New Technologies and Techniques" OBG Management, Feb. 2003. (15 pages).

Dulemba et al. "Use of a Bipolar Electrothermal Vessel Sealer in Laparoscopically Assisted Vaginal Hysterectomy" Sales/Product Literature; Jan. 2004. (1 page).

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000. (1 page).

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000. (4 pages).

Levy et al. "Use of a New Energy-based Vessel Ligation Device During Vaginal Hysterectomy" Int'l Federation of Gynecology and Obstetrics (FIGO) World Congress 1999. (1 page).

Barbara Levy, "Use of a New Vessel Ligation Device During Vaginal Hysterectomy" FIGO 2000, Washington, D.C.. (1 page).

E. David Crawford "Use of a Novel Vessel Sealing Technology in Management of the Dorsal Veinous Complex" Sales/Product Literature 2000. (1 page).

Jarrett et al., "Use of the LigaSure Vessel Sealing System for Peri-Hilar Vessels in Laparoscopic Nephrectomy" Sales/Product Literature 2000. (1 page).

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.. (1 page).

McLellan et al. "Vessel Sealing for Hemostasis During Gynecologic Surgery" Sales/Product Literature 1999. (1 page).

U.S. Appl. No. 08/926,869, filed Sep. 10, 1997; inventor: James G. Chandler.

U.S. Appl. No. 09/177,950, filed Oct. 23, 1998; inventor: Randel A. Frazier.

U.S. Appl. No. 09/387,883, filed Sep. 1, 1999; inventor: Dale F. Schmaltz.

U.S. Appl. No. 09/591,328, filed Jun. 9, 2000; inventor: Thomas P. Ryan.

U.S. Appl. No. 12/336,970, filed Dec. 17, 2008; inventor: Paul R. Sremcich.

Heniford et al. "Initial Research and Clinical Results with an Electrothermal Bipolar Vessel Sealer" Oct. 1999. (1 page).

\* cited by examiner

JAW FORCE CONTROL FOR ELECTROSURGICAL FORCEPS

BACKGROUND

1. Technical Field

The present disclosure relates to electrosurgical forceps and more particularly, to a jaw force control for use with an open bipolar and/or monopolar electrosurgical forceps for sealing, cutting, and/or coagulating tissue.

2. Discussion of Related Art

Electrosurgical forceps utilize both mechanical clamping action and electrical energy to affect hemostasis by heating the tissue and blood vessels to coagulate, cauterize, and/or seal tissue. Electrosurgical forceps may be open forceps for use during open surgical procedures or may be endoscopic forceps for remotely accessing organs through smaller, puncture-like incisions during minimally invasive surgical procedures.

Many surgical procedures require cutting or ligating blood vessels or vascular tissue. By utilizing an electrosurgical forceps, a surgeon can cauterize, coagulate/desiccate, and/or simply reduce or slow bleeding simply by controlling the intensity, frequency, and duration of the electrosurgical energy applied by the jaw members to tissue.

In order to effectively seal vessels (or tissue) at least one of two predominant mechanical parameters must be accurately controlled—the pressure applied to the tissue (vessel) and the gap distance between the electrodes—both of which are affected by the thickness of the tissue before, during, and after sealing. It can be difficult for surgeons to control the pressure between jaw members before and during energy application.

SUMMARY

The present disclosure relates to a surgical instrument that controls the pressure applied to tissue between two jaw members by limiting a closure force of the jaw members. The surgical instrument includes first and second shafts that are pivotal relative to one another to move the jaw members towards a closed configuration. One of the shafts includes a first segment and a second segment that are pivotal relative to one another about a hinge. When the closure force of the jaw members exceeds a predetermined closure force limit, the first segment pivots about the hinge relative to the second segment to prevent the closure force of the jaw members from exceeding the predetermined closure force limit. The hinge may include a resilient member that exerts a closure force to the jaw members when the first segment is pivoted relative to the second segment.

In an aspect of the present disclosure, a surgical instrument includes a first shaft, a second shaft, and a hinge. The first shaft includes a proximal handle and a distal jaw member. The second shaft includes a first segment that has a proximal handle and a second segment that has a distal jaw member. One of the first and second shafts is pivotal relative to the other to pivot the jaw members between an opening configuration where the jaw members are spaced relative to one another and an activatable configuration where the jaw members are closer to one another and suitable for applying electrosurgical energy to tissue disposed therebetween. The hinge couples the first and second segments of the second shaft to one another. The first and second segments have a straight configuration where the first and second segments align with a longitudinal axis that is defined through the second shaft and a pivoted configuration where the second segment is disposed at an angle relative to the longitudinal axis.

In aspects, the hinge biases the first and second segments towards the straight configuration. The first segment may pivot relative to the second segment when a closure force of the jaw members exceeds a threshold closure force. The threshold closure force may be equal to or less than a predetermined closure force limit.

In some aspects, the hinge includes a fastener. The first segment may include a distally extending first flange that defines a first opening that is disposed over or receives the fastener therethrough. The second segment may include a proximally extending second flange that defines a second opening that is disposed over or receives the fastener therethrough.

In certain aspects, the hinge includes a resilient member that is disposed about the fastener between the first and second flanges. The resilient member may be a torsion spring. The resilient member may have a constant or progressive spring rate. The first and second flanges may each define a slot that receives a respective arm of the resilient member. The second flange may define a boss that extends towards the first flange. The boss may define a passage that is coaxial with the second opening and has a diameter that is larger than the second opening. The body of the resilient member may be received within the passage of the boss.

In particular aspects, the first shaft includes a stop that extends from an inner surface of the handle of the first shaft towards the handle of the second shaft. The stop may be configured to prevent the second shaft from pivoting beyond a closed configuration. The second shaft may include a lock that extends from an inner surface of the handle of the second shaft towards the handle of the first shaft. The stop may define an opening and the lock may include a detent that is configured to engage the opening to prevent the second shaft from pivoting towards the open configuration.

In another aspect of the present closure, a method of limiting closure force while grasping tissue with a surgical instrument includes positioning tissue between jaw members of the surgical instrument, moving handles of the first and second shafts of the surgical instrument towards one another to pivot the jaw members towards a closed configuration to apply pressure to tissue disposed between the jaw members, and limiting the pressure to a pressure limit by allowing a first segment of the second shaft to pivot about a common hinge relative to a second segment of the second shaft if the closure pressure exceeds a predetermined pressure limit.

In aspects, the method includes delivering electrosurgical energy with the jaw members to the tissue between the jaw members when the first segment is pivoted relative to the second segment. The method may include abutting a stop of the first shaft with the handle of the second shaft. Additionally or alternatively, the method may include locking the handle of the second shaft to a stop of the first shaft by engaging an opening defined by the stop with a detent of a lock extending from the handle of the second shaft that extends towards the first shaft.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
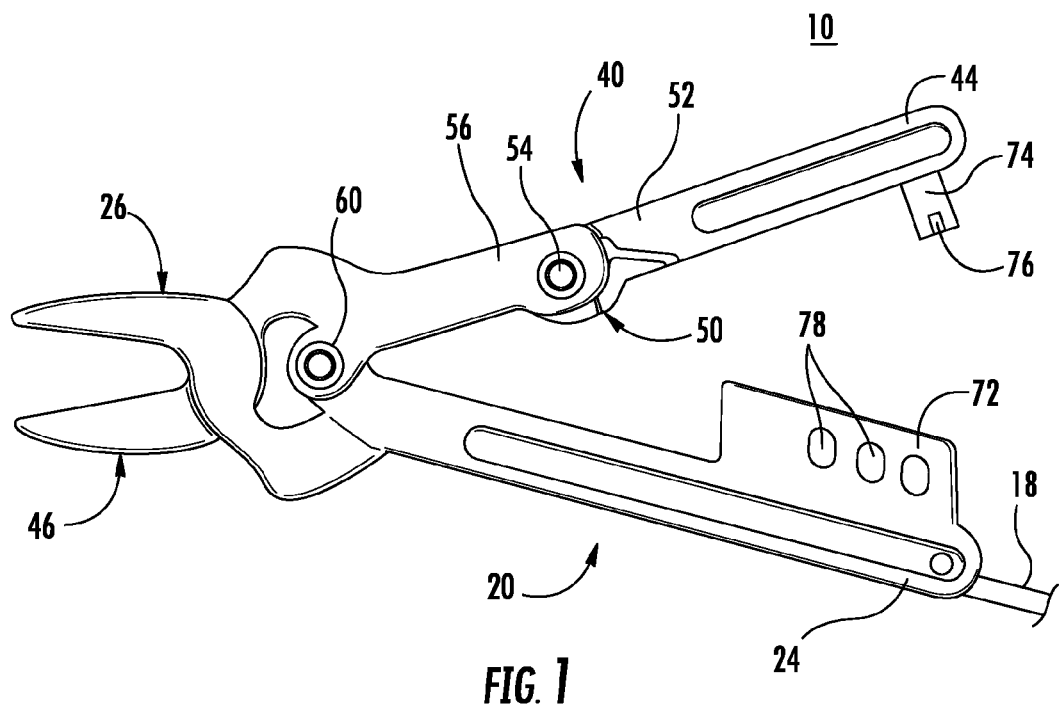
FIG. 1 is a side view of an electrosurgical forceps in accordance with the present disclosure in an open configuration and a pivoting handle in a straight configuration.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a jaw force control for a surgical instrument to limit closure force applied to tissue by jaws members of the surgical instrument. The jaw force control is positioned on one of the shafts of the surgical instrument and includes a resilient member (e.g., a torsion spring) between first and second segments of the shaft of the surgical instrument. As the shafts are moved towards one another, the jaw members are moved towards a closed position and may engage tissue disposed between the jaw members. As the jaw members continue to move towards one another, a closure force is required to compress the tissue disposed between the jaw members so that the jaw members continue to move towards one another. The jaw force control limits this closure force by pivoting the first segment of the shaft relative to the second segment of the shaft when the closure force reaches a predetermined limit. The resilient member is calibrated to maintain the first and second segments in an unpivoted or straight configuration when the closure force is below the predetermined limit and to apply the closure force limit to the first and second jaw members when the first and second segments are pivoted relative to one another. As described herein, the jaw force control is detailed with respect to an open electrosurgical forceps; however, it is contemplated that such a jaw force control may be used in conjunction with other surgical instruments such as a grasper, a dissector, etc.

Referring now to FIG. 1, an open electrosurgical forceps 10 is provided in accordance with the present disclosure and includes a first shaft 20 and a second shaft 40. Each of the first and second shafts 20, 40 has a proximal handle 24, 44 and a distal jaw member 26, 46, respectively.

Figure 2:
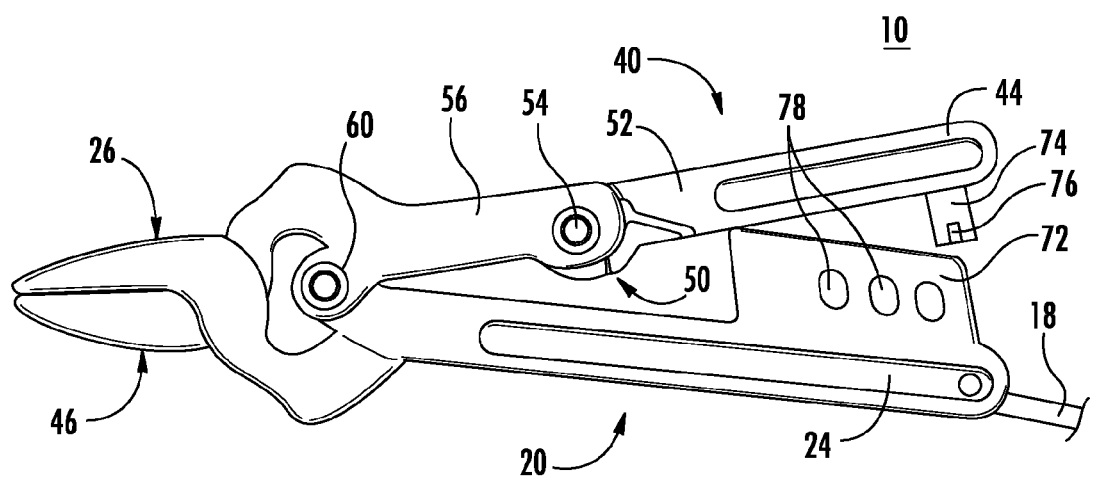
FIG. 2 is a side view of the electrosurgical forceps of FIG. 1 in a closed configuration and the pivoting handle in the straight configuration.

With additional reference to FIG. 2, the shafts 20, 40 are pivotal relative to one another about a pivot 60 between an open configuration (FIG. 1) and a closed configuration (FIG. 2). For the purposes herein, forceps 10 will be described generally. However, the various particular aspects of one envisioned forceps are detailed in U.S. Pat. No. 9,017,372, the entire contents of which are incorporated by reference herein.

The pivot 60 passes through the shafts 20, 40 between the handles 24, 44 and the jaw members 26, 46. The first shaft 20 is in electrical communication with an electrosurgical cable 18 that connects the jaw member 26 to a source of electrosurgical energy. Additionally or alternatively, the second shaft 40 may be in electrical communication with the electrosurgical cable and connects the jaw member 46 to the source of electrosurgical energy.

The second shaft 40 includes a jaw force control 50 that limits the closure force between the jaw members 26, 46 as the jaw members 26, 46 are moved towards the closed configuration. The jaw force control 50 is disposed on the second shaft 40 between the pivot 60 and the handle 44. The jaw force control 50 includes a proximal segment 52 and a distal segment 56 that are pivotally coupled together by a shaft pivot or hinge 54.

Figure 3:
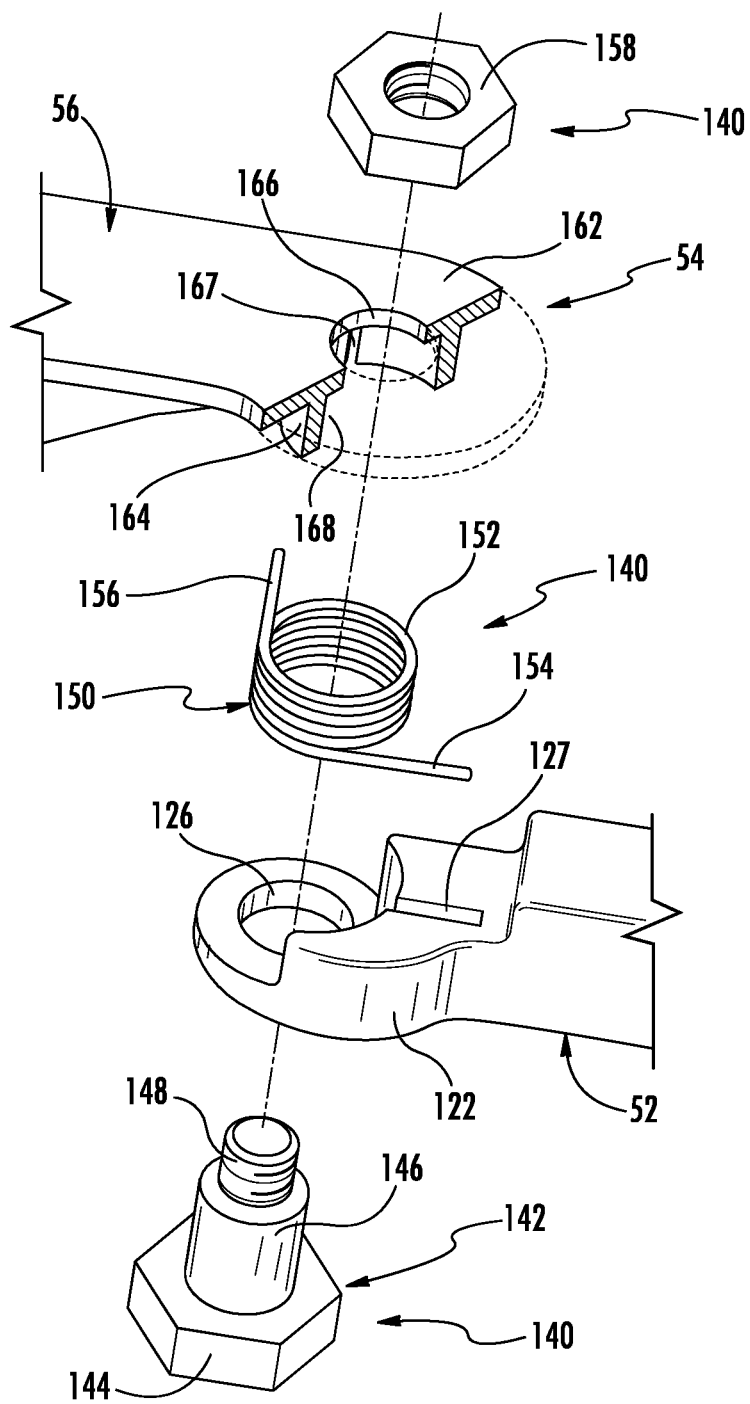
FIG. 3 is an enlarged, exploded view of a hinge of the pivoting handle of FIG. 1.

With reference to FIG. 3, the hinge 54 includes a proximal or first flange 122 that extends from the proximal segment 52, a distal or second flange 162 that extends from the distal segment 56, and a coupling assembly 140. The first flange 122 defines an opening 126 and a slot 127 for receiving portions of the coupling assembly 140. The second flange 162 includes a boss 164 and defines an opening 166 that passes through the boss 164. The boss 164 defines a slot 167 that receives a portion of the coupling assembly 140. The boss 164 also defines a passage 168 that is coaxial with the opening 166 to receive a portion of the coupling assembly 140.

The coupling assembly 140 includes a fastener 142, a resilient member 150, and a securement member 158. The fastener 142 has a head 144, a shank 146, and a threaded portion 148. The resilient member 150 is in the form of a torsion spring with a body 152 that is positioned about the shank 146 of the fastener 142 and includes a first arm 154 and a second arm 156 extending from the body 152.

The fastener 142 passes through the openings 126, 166 of the first and second flanges 122, 162 to pivotally couple the proximal and distal segments 52, 56 of the jaw force control 50 together. The first flange 122 is positioned over the shank 146 of the fastener 142 with the opening 126 of the first flange 122 aligned with the opening 166 of the second flange 162. The head 144 of the fastener 142 is positioned against an outer surface of the first flange 122 with the shank 146 extending through the opening 166 of the second flange 162 such that the shank 146 is disposed substantially within the passage 168 defined in the boss 164. The threaded portion 148 of the fastener 142 extends from the shank 146 through the opening 166 of the second flange 162 with the securement member 158 positioned over the threaded portion 148 to secure the fastener 142 within the openings 126, 166 of the first and second flanges 122, 162, respectively. The securement member 158 is tightened to secure the fastener 142 within the openings 126, 166 while allowing pivotal movement between the first and second flanges 122, 162 of the first and second segments 52, 56, respectively.

The resilient member 150 is disposed over the shank 146 with the body 152 of the resilient member 150 disposed substantially within the passage 168 of the boss 164. The first arm 154 of the resilient member 150 is received in the slot 127 of the first flange 122 and the second arm 156 of the resilient member 150 is received in the slot 167 of the second flange 162. The first and second arms 154, 156 of the resilient member 150 engage walls defining the slots 127, 167 of the first and second segments 52, 56, respectively, to bias the first and second segments 52, 56 towards the straight configuration. In the straight configuration, a longitudinal axis of the first segment 52 substantially aligns with a longitudinal axis of the second segment 56. The first and second flanges 122, 162 are shaped to prevent the first and second segments 52, 56 from over extending beyond an aligned or straight configuration (i.e., the first and second flanges 122, 162 form a mechanical stop).

Figure 4:
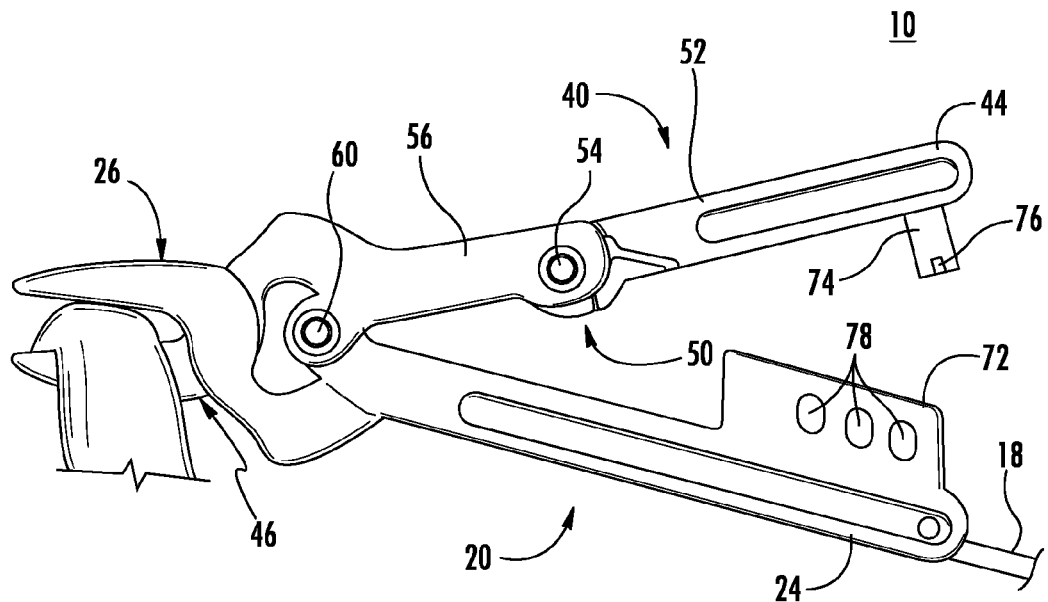
FIG. 4 is a side view of the electrosurgical forceps of FIG. 1 with the pivoting handle in the straight configuration with tissue between the jaws members.
Figure 5:
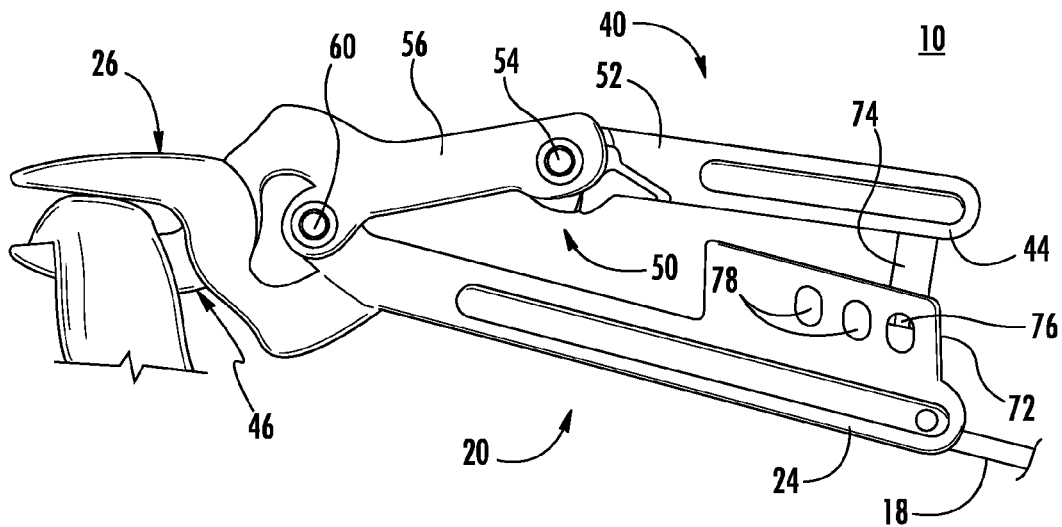
FIG. 5 is a side view of the electrosurgical forceps of FIG. 4 with the pivoting handle in a pivoted configuration.

With additional reference to FIGS. 4 and 5, the resilient member 150 is configured to limit the closure force of the jaw members 26, 46 as the handles 24, 44 are moved toward the closed configuration. The resilient member 150 is sized such that the resilient member 150 prevents the jaws members 26, 46 from applying a pressure greater than a predetermined pressure limit to tissue disposed between the jaw members 26, 46. As shown in FIG. 4, the resilient member 150 urges the proximal and distal segments 52, 56 towards a straight configuration. As the handles 24, 44 are moved toward one another with thick or uncompressible tissue disposed between the jaw members 26, 46, the closure force required to move the jaw members 26, 46 towards the closed configuration exceeds a predetermined closure force limit such that the bias of the resilient member 150 is overcome. When the bias of the resilient member 150 is overcome, the proximal segment 52 pivots relative to the distal segment 56 to pivot towards a pivoted configuration as shown in FIG. 5. In the pivoted configuration, the longitudinal axis of the first segment defines a nonzero angle with the longitudinal axis of the second segment. The pivoting of the proximal segment 52 relative to the distal segment 56 prevents the jaw members 26, 46 from exceeding the predetermined closure force and thus, from applying pressure greater than the predetermined pressure limit to tissue disposed between the jaw members 26, 46. In addition, the bias of the resilient member 150 provides consistent pressure to tissue disposed between the jaw members 26, 46 when the second shaft 40 is in the pivoted configuration.

The pivoting of the proximal segment 52 provides visual and tactile feedback to a clinician that pressure applied to tissue between the jaw members 26, 46 is appropriate for application of electrosurgical energy such that the electrosurgical forceps 10 is in an activatable configuration. The resilient member 150 may have a constant spring rate or a progressive spring rate based on angular deflection of the resilient member 150. When the resilient member 150 has a constant spring rate, the spring rate of the resilient member 150 is sufficient to provide a closure force to the jaw members 26, 46 within the predetermined limit of closure force to provide constant pressure suitable for application of electrosurgical energy to tissue. When the resilient member 150 has a progressive spring rate, the proximal segment 122 remains in the straight configuration when the closure force applied to the jaw members 26, 46 is below a threshold closure force and pivots towards the pivoted configuration when the closure force is greater than the threshold closure force. The threshold closure force is equal to a minimum pressure applied to tissue that is suitable for application of electrosurgical energy to tissue with the jaw members 26, 46. The progressive spring rate of the resilient member 150 has a maximum closure force substantially equal to a force required to reach the predetermined limit of closure force as detailed above.

Referring to FIGS. 4 and 5, as the handles 24, 44 are moved towards each other, the first and second shafts 20, 40 pivot about the pivot 60 such that the jaw members 26, 46 move towards the closed configuration. As the jaw members 26, 46 move towards the closed configuration with a small vessel, or amount of tissue, or a large compressible vessel, or amount of tissue, positioned between the jaw members 26, 46, the closure force of the jaw members 26, 46 applies pressure to the vessel, or tissue until the vessel is compressed between the jaw members 26, 46. If the closure force required to move the jaw members 26, 46 towards the closed configuration is less than or equal to a suitable pressure for application of electrosurgical energy, the jaw members 26, 46 move towards the closed configuration effecting compression of the vessel, or tissue, until the handles 24, 44 are in an approximated or closed position and the jaw members 26, 46 are in an activatable configuration as shown in FIG. 2. In the activatable configuration, the pressure between the jaw members 26, 46 is suitable for application of electrosurgical energy to the vessel, or tissue, between the jaw members 26, 46. If the closure force required to move the jaw members 26, 46 towards the closed configuration would result in pressure suitable for application of electrosurgical energy, the first segment 52 of the second shaft 40 pivots relative to the second segment 56 of the second shaft 40 such that the second shaft 40 is in the pivoted configuration with the jaw members 26, 46 in an activatable configuration as shown in FIG. 5. In such an activatable configuration, the closure force applied to the jaw members 26, 46 is within the predetermined closure force limit such that the jaw members 26, 46 apply pressure for application of electrosurgical energy to the vessel, or tissue, between the jaw member 26, 46.

With particular reference to FIGS. 4 and 5, the first shaft 20 may include a stop 72 that extends towards the second shaft 40 from an inner surface of the handle 24. The stop 72 prevents over rotation or pivoting of the first segment 52 relative to the second segment 56. Specifically, as the first segment 52 is pivoted relative to the second segment 56, the handle 44 abuts the stop 72 to limit pivoting of the first segment 52 relative to the second segment 56.

The second shaft 40 may include lock 74 that extends from an inner surface of the handle 44 towards the first shaft 20. The lock 74 includes a hook or detent 76 and the stop 72 defines one or more openings 78. As shown in FIG. 5, the detent 76 engages the opening 78 of the stop 72 to prevent the first segment 52 of the second shaft 40 from moving away from the first shaft 20 such that the first segment 52 is maintained in position relative to the first shaft 20. In such a configuration, the resilient member 150 may provide a closure force to the jaw members 26, 46 such that the jaw members 26, 46 apply pressure to tissue that is suitable for application of electrosurgical energy.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 6:
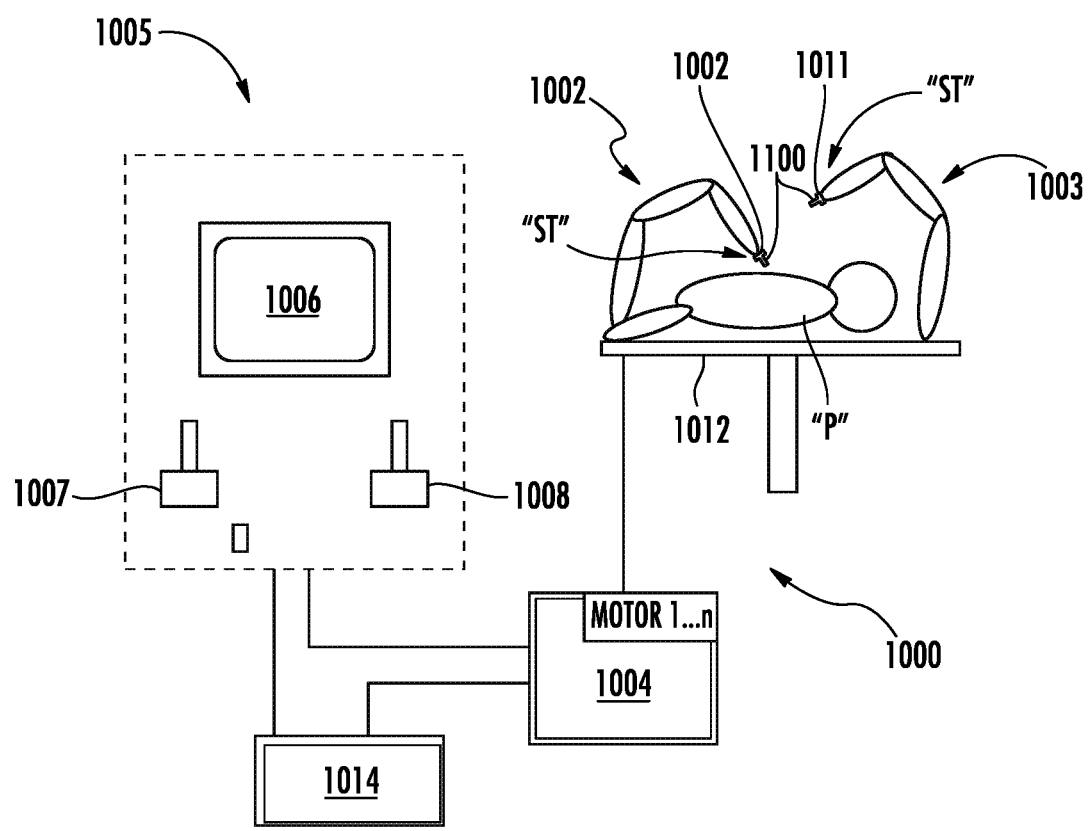
FIG. 6 is a schematic illustration of a medical work station and operating console in accordance with the present disclosure.

Referring also to FIG. 6, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members), in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A medical instrument or surgical tool (including an end effector 1100) may also be attached to the additional robot arm. The medical work station 1000 may include a database 1014 coupled with the control device 1004. In some embodiments, pre-operative data from patient/living being "P" and/or anatomical atlases may be stored in the database 1014.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical instrument, comprising:
    a first shaft defining a first longitudinal shaft axis and having a proximal handle and a distal jaw member, the proximal handle defining a first opening and a second opening, the first and second openings spaced from one another in a direction parallel to the first longitudinal shaft axis;
    a second shaft having a first segment and a second segment, the first segment including a proximal handle of the second shaft and the second segment including a distal jaw member of the second shaft, at least one of the first and second shafts pivotal relative to the other to pivot the jaw members between an open configuration wherein the jaw members are spaced relative to one another and an activatable configuration wherein the jaw members are closer to one another and suitable for applying electrosurgical energy to tissue disposed therebetween;
    a hinge coupling the first segment of the second shaft to the second segment of the second shaft, the first and second segments having a straight configuration wherein the first and second segments align with a second longitudinal shaft axis defined through the second shaft and a pivoted configuration wherein the first segment is disposed at an angle relative to the second longitudinal shaft axis; and
    a lock extending from an inner surface of the handle of the second shaft towards the handle of the first shaft, the lock including a detent configured to be disposed within the first or second opening to prevent the second shaft from pivoting towards the open configuration.

2. The surgical instrument according to claim 1, wherein the hinge biases the first and second segments towards the straight configuration.

3. The surgical instrument according to claim 1, wherein the first segment pivots relative to the second segment when a closure force of the jaw members exceeds a threshold closure force.

4. The surgical instrument according to claim 3, wherein the threshold closure force is equal to a predetermined closure force limit.

5. The surgical instrument according to claim 3, wherein the threshold closure force is less than a predetermined closure force limit.

6. The surgical instrument according to claim 1, wherein the hinge includes a fastener, wherein the first segment includes a distally extending first flange defining a first opening disposed over the fastener, and wherein the second segment includes a proximally extending second flange defining a second opening disposed over the fastener.

7. The surgical instrument according to claim 6, wherein the hinge includes a resilient member disposed about the fastener between the first and second flanges.

8. The surgical instrument according to claim 7, wherein the resilient member is a torsion spring.

9. The surgical instrument according to claim 7, wherein the resilient member has a constant spring rate.

10. The surgical instrument according to claim 7, wherein the resilient member has a progressive spring rate.

11. The surgical instrument according to claim 7, wherein the first and second flanges each define a slot that receive a respective arm of the resilient member.

12. The surgical instrument according to claim 7, wherein the second flange defines a boss that extends towards the first flange, the boss defining a passage coaxial with the second opening and having a diameter larger than the second opening.

13. The surgical instrument according to claim 12, wherein a body of the resilient member is received within the passage of the boss.

14. The surgical instrument according to claim 1, wherein the first shaft includes a stop extending from an inner surface of the handle of the first shaft towards the handle of the second shaft, the stop configured to prevent the second shaft from pivoting beyond a closed configuration.

15. The surgical instrument according to claim 14, wherein the first and second openings are defined in the stop.

16. A method of limiting closure force while grasping tissue with a surgical instrument, the method comprising:
    positioning tissue between jaw members of the surgical instrument;
    moving handles of first and second shafts of the surgical instrument towards one another to pivot the jaw members towards a closed configuration to apply pressure to tissue disposed between the jaw members;
    limiting the pressure to a predetermined pressure limit by allowing a first segment of the second shaft to pivot about a common hinge relative to a second segment of the second shaft if the closure pressure exceeds the predetermined pressure limit; and
    locking the surgical instrument in the closed configuration by engaging a first opening or a second opening defined in the first shaft with a detent of a lock extending from the second handle towards the first handle, the first and second openings spaced apart from one another in a direction parallel to a first longitudinal shaft axis defined by the first shaft.

17. The method according to claim 16, further comprising delivering electrosurgical energy with the jaw members to the tissue between the jaw members when the first segment is pivoted relative to the second segment.

18. The method according to claim 16, further comprising abutting a stop of the first shaft with the handle of the second shaft.

* * * * *